(12) United States Patent
Balaya et al.

(10) Patent No.: US 8,754,215 B2
(45) Date of Patent: Jun. 17, 2014

(54) PROCESS FOR THE PREPARATION OF PRAZIQUANTEL

(71) Applicant: Sequent Scientific Limited, Bangalore (IN)

(72) Inventors: Lingappa Balaya, Mangalore (IN); Mahalinga Manjathuru, Mangalore (IN); Yogeesh Derambala, Mangalore (IN); Pejakala Kakrannaya Vasudeva, Mangalore (IN); Thangavel Arulmoli, Mangalore (IN)

(73) Assignee: Sequent Scientific Limited, Bangalore, IN (US)

( * ) Notice: Subject to any disclaimer, the term of this patent is extended or adjusted under 35 U.S.C. 154(b) by 0 days.

(21) Appl. No.: 13/916,395

(22) Filed: Jun. 12, 2013

(65) Prior Publication Data

US 2013/0289275 A1    Oct. 31, 2013

Related U.S. Application Data

(63) Continuation-in-part of application No. PCT/IN2011/000846, filed on Dec. 12, 2011.

(51) Int. Cl.
*C07D 241/38* (2006.01)
*C07C 237/02* (2006.01)

(52) U.S. Cl.
USPC .......................................... 544/344; 564/164

(58) Field of Classification Search
CPC ..... C07C 237/24; C07C 231/14; C07D 471/06
See application file for complete search history.

(56) References Cited

U.S. PATENT DOCUMENTS

| 3,071,613 | A | | 1/1963 | Surrey |
| 4,049,659 | A | | 9/1977 | Pohike |
| 4,866,056 | A | * | 9/1989 | Dorgan et al. ............. 514/211.1 |

OTHER PUBLICATIONS

Laurent, S.A., et al. "Synthesis of 'Trioxaquantel' Derivatives as Potential New Antischistosomal Drugs." Eur. J. Org. Chem. (2008), pp. 895-913.*
Kim, J.H., et al. "Formation of Pyrazinoisquinoline Ring System by the Tandem Amidoalkylation and N-Acyliminium Ion Cyclization: An Efficient Synthesis of Praziquantel." Tetrahedron. (1998), vol. 54, pp. 7395-7400.*
"International Search Report issued for PCT/IN2011/000846 dated Jul. 17, 2012".
Torrado, et al., "Preparation, Dissolution and Characterization fo Praziquantel Solid Dispersions", Chem. Pharm. Bull., 1999, vol. 47, 11, 1629-1633.

* cited by examiner

*Primary Examiner* — Noble Jarrell
*Assistant Examiner* — John S Kenyon
(74) *Attorney, Agent, or Firm* — Kramer Amado, P.C.

(57) ABSTRACT

The present disclosure describes a novel, cost-effective process for preparation of a 4-oxo-1,2,3,6,7,11b-hexahydro-4H-pyrazino-[2,1-a]isoquinoline derivatives. Specifically, it discloses a process for the preparation of the anthelmintic drug praziquantel through the use of a novel intermediate, 2-[(2,2-dimethoxyethyl)benzyl amino]-N-phenethylacetamide. This present disclosure also describes a novel crystalline form of 4-oxo-1,2,3,6,7,11b-hexahydro-4H-pyrazino[2,1-a]isoquinoline.

9 Claims, 2 Drawing Sheets

Figure1: X-Ray diffractogram of 4-oxo-1,2,3,6,7,11b-hexahydro-4H-pyrazino[2,1-a]isoquinoline of formula II
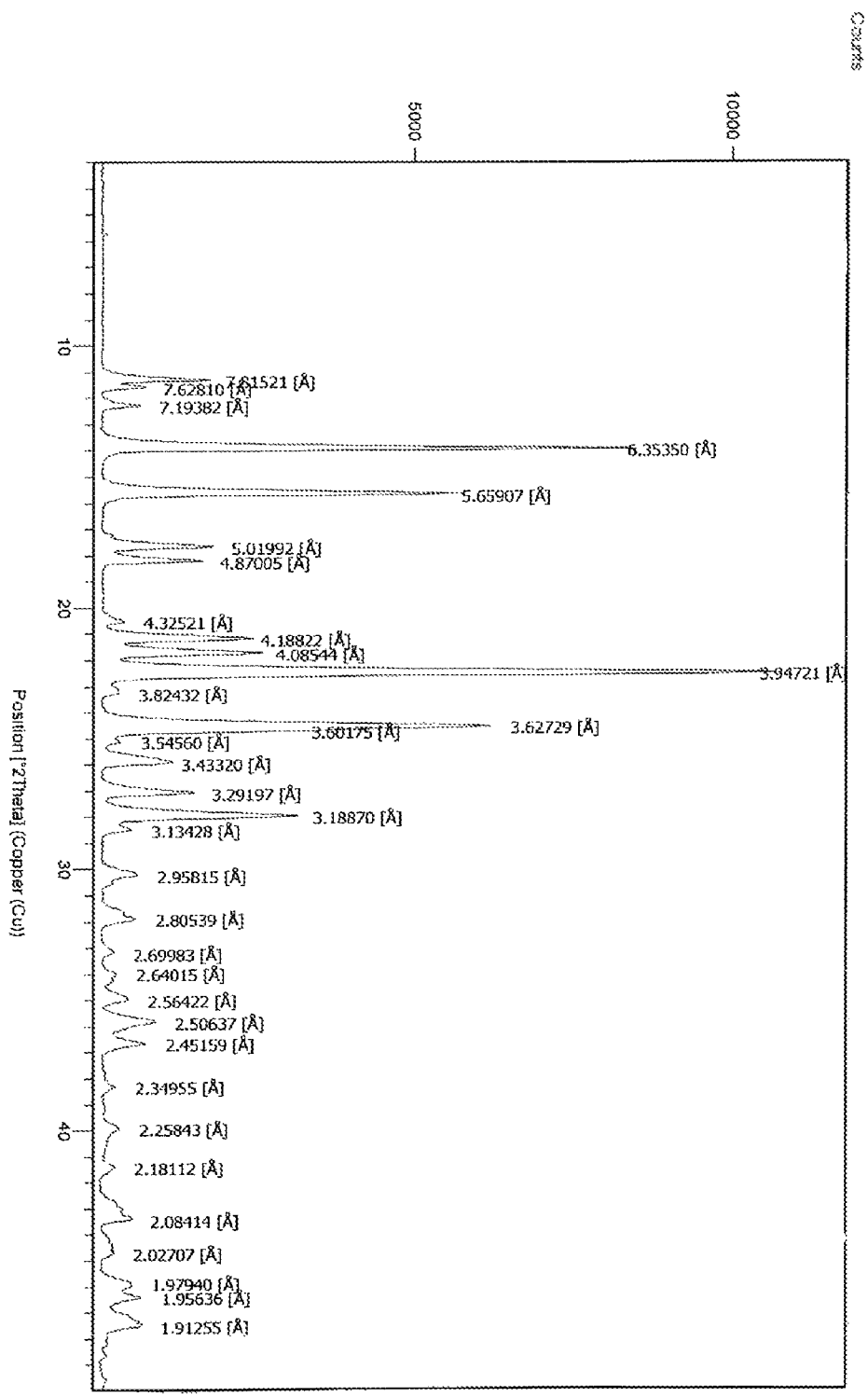

Figure 2: X-Ray diffractogram of Praziquantel of formula I
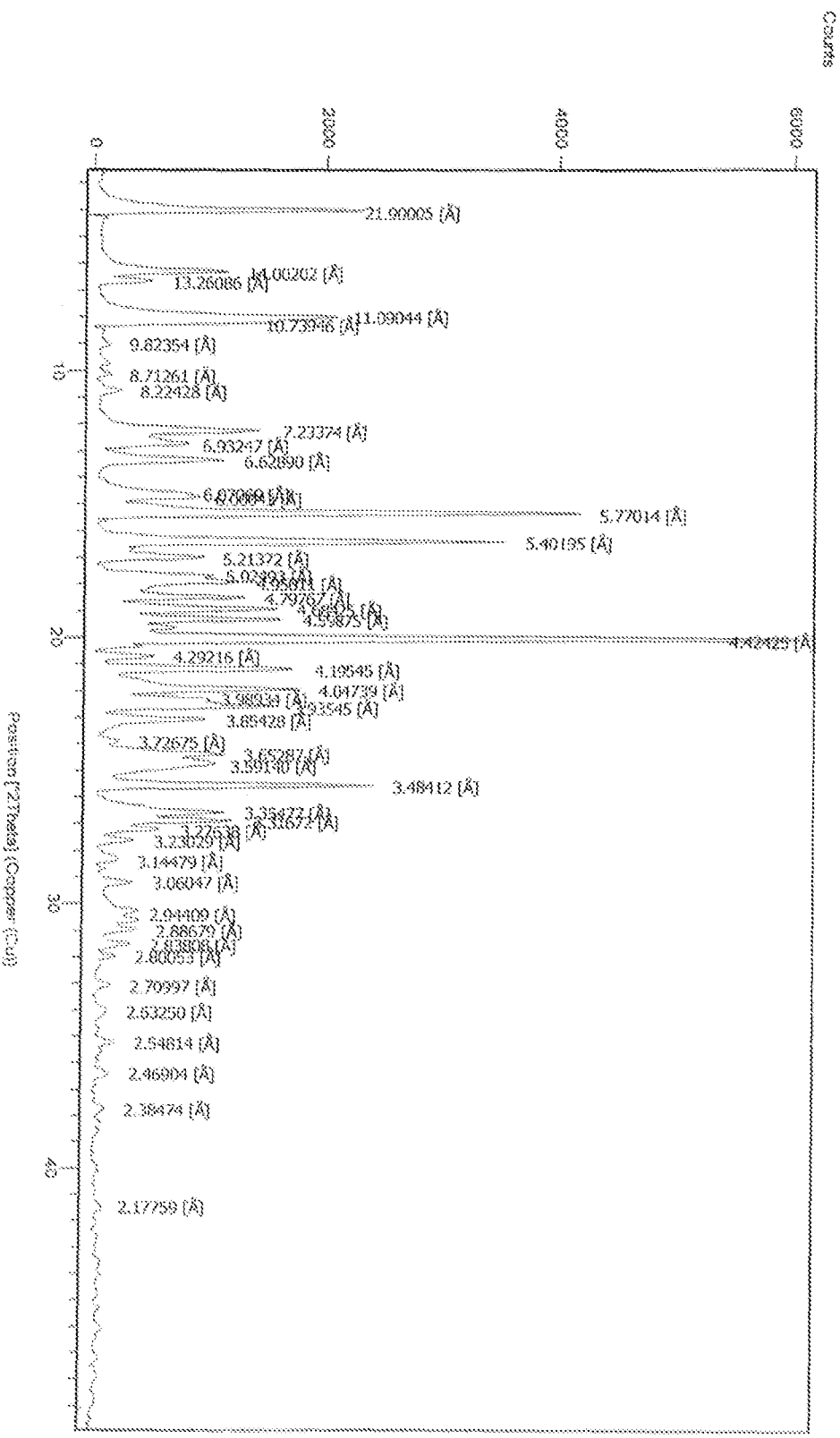

PROCESS FOR THE PREPARATION OF PRAZIQUANTEL

CROSS-REFERENCE TO RELATED APPLICATIONS

This application is a continuation-in-part of parent International Application No. PCT/IN2011/000846, filed on Dec. 12, 2011 and published as WO 2012/081035, which claims priority to Indian patent application IN 3794/CHE/2010, filed on Dec. 13, 2010. The entire disclosure of each prior application is hereby incorporated by reference in its entirety.

BACKGROUND

The present disclosure relates to a novel, cost-effective process for preparation of a 4-oxo-1,2,3,6,7,11b-hexahydro-4H-pyrazino-[2,1-a]isoquinoline derivatives. Specifically, it relates to a process for the preparation of praziquantel involving new intermediate.

Praziquantel of formula I, having the chemical name 2-cyclohexylcarbonyl-4-oxo-1,2,3,6,7,11b-hexahydro-4H-pyrazino[2,1-a]isoquinoline, is a member of the 2-acyl-4-oxopyrazinoisoquinoline compounds, which are used as drugs for the treatment of a variety of worm infections. Praziquantel is primarily used against parasites known as "cestodes" and it is also effective against flukes.

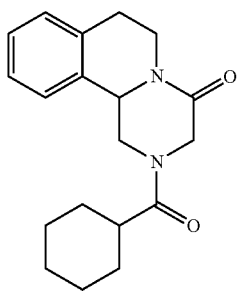

(I)

There are number of literature references which describe the process for preparation of praziquantel. U.S. Pat. No. 4,001,411 describes a process for preparation of praziquantel by acylating 4-oxo-1,2,3,6,7,11b-hexahydro-4H-pyrazino[2,1-a]isoquinoline with cyclohexanoylchloride in chloroform and triethylamine.

KR2002076486 describes a process for preparation of praziquantel by reacting phenylethylamine with chloroacetyl chloride to obtain 2-chloro-N-phenethylacetamide. The compound 2-chloro-N-phenethylacetamide is then reacted with pthalimide to give 2-pthalimido-N-phenethylacetamide, which is then treated with hydrazine monohydrate to give 2-amino-N-phenylethylacetamide. On further treatment with bromoacetal, 2-amino-N-phenylethylacetamide gives 2-[2,2-dimethoxyethyl)amino]-N-(2-phenylethyl)acetamide. This compound on further cyclization and acylation using cyclohexanoylchloride forms praziquantel.

CN1683346 describes a similar above process except the first step where 2-amino-N-phenylethylacetamide is prepared by reacting 2-aminoacetylchloride hydrochloride with phenylethylamine.

WO2009115333 describes many processes in one of which 3-phenylpropanenitrile is reacted with aminoacetal in presence of formaldehyde to obtain 2-[(2,2-dialkoxyethyl)amino]-N-(2-phenylethyl)acetamide, which is further cyclised and acylated using cyclohexanoylchloride to form praziquantel.

*Eur. J. Org. Chem.* 2008, 895-913 describes a process comprising: a) reacting phenylethylamine with chloroacetyl chloride in presence of sodium bicarbonate to obtain 2-chloro-N-phenethylacetamide, b) treating 2-chloro-N-phenethylacetamide with aminoacetaldehyde dimethylacetal to give 2-[2,2-dimethoxyethyl)amino]-N-(2-phenylethyl)acetamide, c) making hydrochloride salt of 2-[(2,2-dimethoxyethyl)amino]-N-(2-phenylethyl)acetamide, and d) cyclising using sulphuric acid to form praziquanamine (i.e.4-oxo-1,2,3,6,7,11b-hexahydro-4H-pyrazino[2,1-a]isoquinoline).

A major drawback in above the known processes is the use of aminoacetaldehyde dimethylacetal, a very expensive raw material. Moreover, it is used in two equivalents, with one equivalent being consumed in the reaction and the other equivalent being lost. It poses a lot of concern in terms of cost at the commercial scale production.

Thus there is a need to develop a process for the preparation of Praziquantel, which is cost effective and easy to handle on a commercial scale. In particular, there is a need to develop a process which avoids the use of costly aminoacetaldehyde dimethylacetal compounds to reduce the overall cost of production.

Thus, the present disclosure provides a cost effective process for preparing Praziquantel in good yield and good purity on a commercial scale.

SUMMARY

Various embodiments disclosed herein provide a process for the preparation of 2-[2,2-dimethoxyethyl)amino]-N-(2-phenylethyl)acetamide of formula III, presented in Scheme I. An exemplary process of making the compound of formula III is illustrated in Scheme I, and comprises:

a) condensation of β-phenylethylamine with chloroacetyl chloride in the presence of a solvent and a base to obtain 2-chloro-N-phenethylacetamide of formula V;

b) condensation of benzylamine with chloroacetaldehyde dimethylacetal in presence of water and a base to obtain N-benzyl-2,2-dimethoxyethanamine of formula VI;

c) condensation of 2-chloro-N-phenethylacetamide of formula V prepared in step a) with N-benzyl-2,2-dimethoxyethanamine of formula VI prepared in step b) in presence of water and a base to obtain 2-[(2,2-dimethoxyethyl)benzylamino]-N-phenethylacetamide of formula IV; and d) reduction of 2-[2,2-dimethoxyethyl)benzylamino]-N-phenethylacetamide of formula IV using a reducing agent and a solvent in presence of hydrogen to obtain 2-[(2,2-dimethoxyethyl)amino]-N-(2-phenylethyl)acetamide of formula III.

SCHEME I

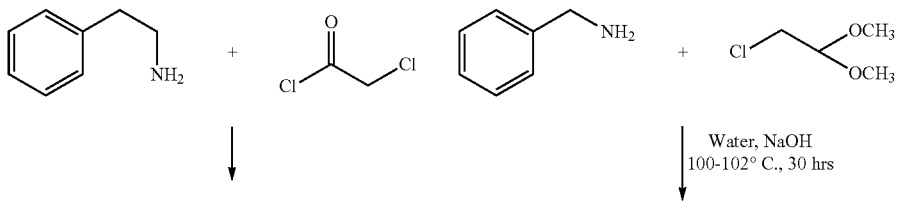

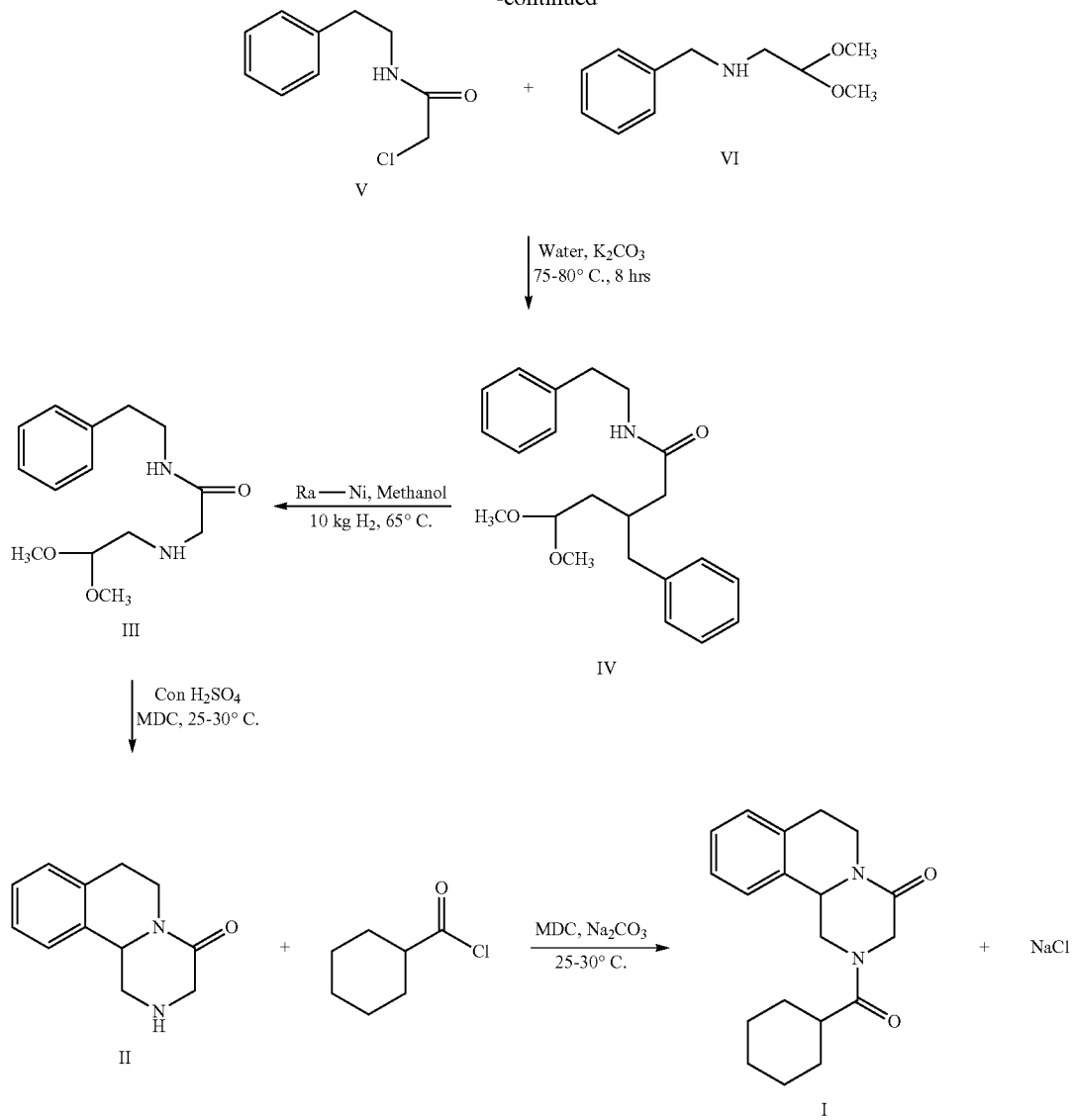

Various embodiments disclosed herein provide a process for the preparation of Praziquantel of formula I. An exemplary process of making Praziquantel of formula I is illustrated in Scheme I, and comprises:

a) condensation of β-phenylethylamine with chloroacetyl chloride in presence of a solvent and a base to obtain 2-chloro-N-phenethylacetamide of formula V;

b) condensation of Benzylamine with chloroacetaldehyde dimethylacetal in presence of water and a base to obtain N-benzyl-2,2-dimethoxyethanamine of formula VI;

c) condensation of 2-chloro-N-phenethylacetamide of formula V prepared in step a) with N-benzyl-2,2-dimethoxyethanamine of formula VI prepared in step b) in presence of water and a base to obtain 2-[(2,2-dimethoxyethyl)benzylamino]-N-phenethylacetamide of formula IV;

d) reduction of 2-[(2,2-dimethoxyethyl)benzylamino]-N-phenethylacetamide of formula IV using a reducing agent and a solvent in presence of hydrogen to obtain 2-[(2,2-dimethoxyethyl)amino]-N-(2-phenylethyl)acetamide of formula III;

e) cyclisation of 2-[(2,2-dimethoxyethyl)amino]-N-(2-phenylethyl)acetamide of formula III prepared in step d) using an acid in the presence of a solvent to obtain 4-oxo-1,2,3,6,7,11b-hexahydro-4H-pyrazino[2,1-a]isoquinoline of formula II; and f) acylation of 4-oxo-1,2,3,6,7,11b-hexahydro-4H-pyrazino[2,1-a]isoquinoline of formula II with cyclohexanoylchloride in presence of a base and a solvent to obtain Praziquantel of formula I.

Further embodiments disclosed herein provide a process for the preparation of Praziquantel of formula I by cyclisation of 2-[(2,2-dimethoxyethyl)amino]-N-(2-phenylethyl)acetamide using an acid in the presence of a solvent to obtain 4-oxo-1,2,3,6,7,11b-hexahydro-4H-pyrazino[2,1-a]isoquinoline; and acylation of 4-oxo-1,2,3,6,7,11b-hexahydro-4H-pyrazino[2,1-a]isoquinoline with cyclohexanoylchloride in presence of a base and a solvent to obtain Praziquantel.

Certain embodiments disclosed herein relate to the novel compound 2-[(2,2-dimethoxyethyl)benzyl amino]-N-phenethylacetamide of formula IV. The compound of formula IV is a useful precursor for 2-[(2,2-dimethoxyethyl)amino]-N-(2-phenylethyl)acetamide of formula III and a useful intermediate for Praziquantel I.

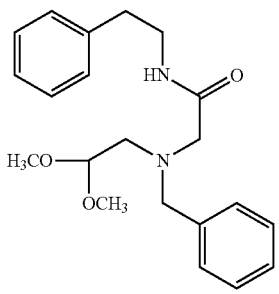

IV

Various embodiments disclosed herein provide a novel crystalline form of 4-oxo-1,2,3,6,7,11b-hexahydro-4H-pyrazino[2,1-a]isoquinoline of formula II which is very stable. This novel crystalline form is characterised by an X-Ray powder diffractogram substantially as given in FIG. 1. In various embodiments, the novel crystalline form of 4-oxo-1,2,3,6,7,11b-hexahydro-4H-pyrazino[2,1-a]isoquinoline is obtained by crystallizing 4-oxo-1,2,3,6,7,11b-hexahydro-4H-pyrazino[2,1-a]isoquinoline from ethyl acetate.

BRIEF DESCRIPTION OF THE DRAWINGS

In order to better understand various exemplary embodiments, reference is made to the accompanying drawings, wherein:

FIG. 1 shows an X-Ray diffractogram of 4-oxo-1,2,3,6,7,11b-hexahydro-4H-pyrazino[2,1-a]isoquinoline; and FIG. 2 shows an X-Ray diffractogram of Praziquantel.

DETAILED DESCRIPTION

Accordingly, in various embodiments disclosed herein, the condensation of β-phenylethylamine with chloroacetylchloride is carried out in presence of an organic solvent preferably an aromatic solvent more preferably selected from benzene or substituted benzene or toluene, most preferably toluene and a base selected from an alkali metal carbonate or bicarbonate preferably selected from sodium carbonate, sodium bicarbonate, potassium carbonate and potassium bicarbonate, more preferably sodium bicarbonate, in the temperature range −5 to 15° C., preferably in the range 0 to 10° C.

In certain embodiments disclosed herein, the condensation in step b) is carried out in an aqueous solvent, preferably water and a base selected from sodium hydroxide or potassium hydroxide, preferably sodium hydroxide, in the temperature range 95 to 105° C., preferably at 100-102° C. to obtain N-benzyl-2,2-dimethoxyethanamine.

In some embodiments disclosed herein, the condensation in step c) is carried out in an aqueous solvent, preferably water and a base selected from sodium carbonate or sodium bicarbonate or potassium carbonate preferably potassium carbonate, in the temperature range 70 to 90° C., preferably at 75 to 80° C.

In various embodiments disclosed herein, the reduction in step d) is carried out in an alcoholic solvent like methanol, ethanol, isopropanol, preferably in the presence of methanol using a reducing agent selected from Raney nickel, Palladium on carbon or Platinum, preferably Raney nickel. The reduction is preferably carried out at 10 kg $H_2$ pressure and at a temperature of about 65° C. to obtain 2-[(2,2-dimethoxyethyl)amino]-N-(2-phenylethyl)acetamide.

In some embodiments disclosed herein, the cyclization of 2-[(2,2-dimethoxyethyl)amino]-N-(2-phenylethyl)acetamide is carried out in presence of an acid, preferably mineral acid, more preferably concentrated sulphuric acid and in presence of an organic solvent selected from dichloromethane or dichloroethane or chloroform or carbon tetrachloride preferably dichloromethane. Preferably in the temperature range 25 to 30° C. to obtain 4-oxo-1,2,3,6,7,11b-hexahydro-4H-pyrazino[2,1-a]isoquinoline of formula II.

In certain embodiments disclosed herein, the acylation of 4-oxo-1,2,3,6,7,11b-hexahydro-4H-pyrazino[2,1-a]isoquinoline of formula II is carried out in presence of a base, preferably sodium carbonate and in presence of an organic solvent selected from dichloromethane or dichloroethane or chloroform or carbon tetrachloride preferably dichloromethane. Preferably in the temperature range 25 to 30° C. to obtain Praziquantel.

In various embodiments disclosed herein, 4-oxo-1,2,3,6,7,11b-hexahydro-4H-pyrazino[2,1-a]isoquinoline of formula II is obtained in a novel crystalline form which is very stable. The novel crystalline form of 4-oxo-1,2,3,6,7,11b-hexahydro-4H-pyrazino[2,1-a]isoquinoline is obtained by recrystallization from ethyl acetate. This novel crystalline 4-oxo-1,2,3,6,7,11b-hexahydro-4H-pyrazino[2,1-a]isoquinoline is represented by an X-ray diffractogram substantially as given in FIG. 1. The novel crystalline 1,2,3,6,7,11b-hexahydro-4H-pyrazino[2,1-a]isoquinoline of formula II is further characterized by its X-ray powder diffractogram.

The X-ray powder diffractogram of 4-oxo-1,2,3,6,7,11b-hexahydro-4H-pyrazino[2,1-a]isoquinoline of formula II exhibits peaks in at least 5 of the following positions: 11.3224±0.2 2θ, 11.6010±0.2 2θ, 12.3040±0.2 2θ, 13.9389±0.2 2θ, 15.6595±0.2 2θ, 17.6684±0.2 2θ, 18.2167±0.2 2θ, 20.5348±0.2 2θ, 21.2141±0.2 2θ, 21.7543±0.2 2θ, 22.5259±0.2 2θ, 23.2597±0.2 2θ, 24.5423±0.2 2θ, 24.7190±0.2 2θ, 25.1168±0.2 2θ, 25.9533±0.2 2θ, 27.0875±0.2 2θ, 27.9823±0.2 2θ, 28.4783±0.2 2θ, 30.2130±0.2 2θ, 31.9009±0.2 2θ, 33.1835±0.2 2θ, 33.9561±0.2 2θ, 34.9936±0.2 2θ, 35.8283±0.2 2θ, 36.6569±0.2 2θ, 38.3095±0.2 2θ, 39.9195±0.2 2θ, 41.3981±0.2 2θ, 43.4197±0.2 2θ, 44.7071±0.2 2θ, 15.8443±0.2 2θ, 46.4157±0.2 2θ, and 47.5018±0.2 2θ.

In various embodiments, the X-ray powder diffractogram of 4-oxo-1,2,3,6,7,11b-hexahydro-4H-pyrazino[2,1]-isoquinoline exhibits peaks in each of the following five positions: 13.9389±0.2 2θ, 15.6595±0.2 2θ, 22.5259±0.2 2θ, 24.5423±0.2 2θ, and 27.9823±0.2 2θ. In certain embodiments, the X-ray powder diffractogram of 4-oxo-1,2,3,6,7,11b-hexahydro-4H-pyrazino[2,1-a]isoquinoline exhibits peaks in each of the following ten positions: 11.3224±0.2 2θ, 13.9389±0.2 2θ, 15.6595±0.2 2θ, 17.6684±0.2 2θ, 18.2167±0.2 2θ, 21.2141±0.2 2θ, 21.7543±0.2 2θ, 22.5259±0.2 2θ, and 24.5423±0.2 2θ, 27.9823±0.2 2θ.

In further embodiments disclosed herein, praziquantel is crystallized from a mixed acetone/water solvent to produce praziquantel as a crystalline product. In other embodiments disclosed herein, praziquantel is crystallized from methanol to produce praziquantel as a crystalline product.

In various embodiments disclosed herein, praziquantel of formula I obtained by crystallization from either acetone/water or methanol is crystalline in nature and is characterized by an X-ray diffractogram substantially as shown in FIG. 2. The X-ray powder diffractogram of praziquantel crystallized from either acetone/water or methanol exhibits peaks in at least 5 of the following positions: 4.0347±0.2 2θ, 6.3125, 6.6657±0.2 2θ, 7.9721±0.2 2θ, 8.2331±0.2 2θ, 9.0022±0.2

2θ, 10.1529±0.2 2θ, 10.7575±0.2 2θ, 12.2359±0.2 2θ, 12.7698±0.2 2θ, 13.3571±0.2 2θ, 14.5918±0.2 2θ, 14.7636±0.2 2θ, 15.3563±0.2 2θ, 16.4099±0.2 2θ, 17.0067±0.2 2θ, 17.6506±0.2 2θ, 17.9196±0.2 2θ, 18.4939±0.2 2θ, 18.9457±0.2 2θ, 19.3013±0.2 2θ, 20.0703±0.2 2θ, 20.6947±0.2 2θ, 21.1772±0.2 2θ, 21.9613±0.2 2θ, 22.2849±0.2 2θ, 22.5941±0.2 2θ, 23.0764±0.2 2θ, 23.8775±0.2 2θ, 24.3678±0.2 2θ, 34.7914±0.2 2θ, 25.5675±0.2 2θ, 26.5709±0.2 2θ, 26.8815±0.2 2θ, 27.2188±0.2 2θ, 27.6148±0.2 2θ, 28.3811±0.2 2θ, 29.1801±0.2 2θ, 30.3608±0.2 2θ, 30.9784±0.2 2θ, 31.5238±0.2 2θ, 31.9577±0.2 2θ, 33.0558±0.2 2θ, 34.0577±0.2 2θ, 35.2215±0.2 2θ, 36.3888±0.2 2θ, 37.7226±0.2 2θ, and 41.4325±0.2 2θ.

In various embodiments, the X-ray powder diffractogram of praziquantel of formula I obtained by crystallization from either acetone/water or methanol exhibits peaks in five of the following positions: 4.0347±0.2 2θ, 7.9721±0.2 2θ, 15.3563±0.2 2θ, 16.4099±0.2 2θ, 20.0703±0.2 2θ, and 25.5675±0.2 2θ. In certain embodiments, the X-ray powder diffractogram of 4-oxo-1,2,3,6,7,11b-hexahydro-4H-pyrazino[2,1-a]isoquinoline exhibits peaks in ten of the following positions: 4.0347±0.2 2θ, 7.9721±0.2 2θ, 12.2359±0.2 2θ, 13.3571±0.2 2θ, 15.3563±0.2 2θ, 16.4099±0.2 2θ, 18.4939±0.2 2θ, 18.9457±0.2 2θ, 19.3013±0.2 2θ, 20.0703±0.2 2θ, 21.1772±0.2 2θ, 21.9613±0.2 2θ, 22.5941±0.2 2θ, and 25.5675±0.2 2θ.

The process of making praziquantel disclosed herein avoids the use of the expensive raw material aminoacetaldehyde dimethylacetal. Instead, the process of making praziquantel disclosed herein produces a novel intermediate compound, 2-[(2,2-dimethoxyethyl)benzylamino]-N-phenethylacetamide, in water. Production of this intermediate compound is very inexpensive. Use of this intermediate compound to make praziquantel reduces the overall cost of the praziquantel significantly. Apart from this the present process uses water as a solvent in multiple steps, which makes the process disclosed herein green and environmentally friendly.

The process of making praziquantel disclosed herein can be illustrated by the following examples, which are not intended to limit the scope of invention.

Example 1

Preparation of 2-cyclohexylcarbonyl-4-oxo-1,2,3,6,7,11b-hexahydro-4H-pyrazino[2,1-a]isoquinoline (a) Preparation of 2-chloro-N-phenethylacetamide β-phenylethylamine (0.68 kg) was taken in dry toluene (4.42 L) and sodium bicarbonate (0.612 kg) was added at 30° C. and cooled to 0-5° C. Chloroacetyl chloride was slowly added under nitrogen blanket at 0-10° C., stirred and maintained for 2 hr. After completion of the reaction, water was added slowly and reaction mass was allowed to attain 33±2° C. and the layers were separated. To the aqueous layer toluene was added, stirred and two layers were separated. To the organic layer dil HCl solution (0.653 L DM water+0.272 L con HCl) was added, stirred and two layers were separated. To the organic layer again sodium bicarbonate solution (0.653 L DM water+0.068 kg sodium bicarbonate) was added, stirred and two layers were separated. Water was added to the organic layer, stirred and two layers were separated. From the organic layer toluene was distilled out, methanol was added, heated to 58° C., stirred. To the reaction mass water was added, temperature was maintained at 58° C., stirred for 1-1.5 hr, cool to 30±2° C. for 3 hrs under stirring. Stirring was continued for 3 hrs at 0-5° C. The reaction mass was filtered, washed with water and dried.

Yield: 1 kg.

(b) Preparation of N-benzyl-2,2-dimethoxyethanamine

Benzylamine (0.927 kg), chloroacetaldehydedimethylacetal (0.909 kg), sodium hydroxide solution (0.35 kg) in 2.72 L of water were charged into the flask under stirring at 25-30° C. for 10-15 min. Reaction mass was heated to 100-102° C. under stirring for 30 hrs. After completion of reaction, reaction mass was allowed to settle for 30 min. Two layers are separated and upper product layer was collected, distilled under high vacuum.

Yield: 1.0 kg.

(c) Preparation of 2-[(2,2-dimethoxyethyl)benzylamino]-N-phenethylacetamide

Prazole-1 (0.589 kg), Prazole-2 (0.614 kg), potassium carbonate (0.522 kg) in 1.84 L of water were charged into the flask under stirring at 25-30° C. for 10-15 min. Reaction mass was heated to 75-80° C. under stirring for 8 hrs. After completion of reaction, TLC was checked. The reaction mass was cooled, Toluene was added and reaction mass was allowed to attain 30±2° C. for 15 min under stirring. Two layers were separated. To the toluene layer 10% acetic acid solution (0.55 L DM water+0.0614 L acetic acid) was added, stirred and two layers were separated. To the organic layer again 10% acetic acid solution (0.55 L DM water+0.0614 L acetic acid) was added, stirred and two layers were separated. To the organic layer 5% sodium bicarbonate solution (0.614 L DM water+0.0307 kg sodium bicarbonate) was added, stirred and two layers were separated. To the organic layer again 5% sodium bicarbonate solution (0.614 L DM water+0.0307 kg sodium bicarbonate) was added, stirred and two layers were separated. To the organic layer DM water was added, stirred and two layers were separated. From the organic layer toluene was distilled out under vacuum below 60° C., material was collected.

Yield: 1.0 kg.

(d) Preparation of 2-[(2,2-dimethoxyethyl)amino]-N-(2-phenylethyl)acetamide

Prazole-3 (1.47 kg), methanol (4.41 L) were treated with Raney nickel (0.147 kg) at 25-30° C. Flush nitrogen and hydrogen. 10 kg/cm$^2$ Hydrogen pressure was applied at 25-30° C. Reaction mass was heated to 65-67° C. for 20 hrs at 10 kg hydrogen pressure. After completion of reaction, reaction mass was cooled to room temperature, filtered and washed with methanol. Methanol and toluene were distilled out under vacuum below 55° C., thick oil was collected.

Yield: 1.0 kg.

(e) Preparation of 4-oxo-1,2,3,6,7,11b-hexahydro-4H-pyrazino[2,1-a]isoquinoline

Prazole-4 (2.0 Kg), dichloromethane (4.0 L) and sulphuric acid (2.33 L) were stirred at 10-15° C. for 30 min, slowly allowed to attain 25-30° C. and stirred for 2 hrs. After completion of reaction, reaction mass was quenched to pre-cooled DM water at 0-10° C. Two layers were separated. Aqueous layer was washed with dichloromethane, pH was adjusted to 6.5-7 using 20% sodium hydroxide solution (2.6 kg sodium hydroxide+13.0 L DM water), stirred for 10 min. Allowed the reaction mass to attain 25-30° C. Dichloromethane was added to the above solution, stirred and two layers were separated. Aqueous layers were twice extracted with Dichloromethane. Combined organic layers were washed with DM water, brine solution, dried. Carbon treatment was given to organic layer, stirred and Dichloromethane was distilled. Crude material was crystallized by ethyl acetate.

Yield: 1.0 kg.

(f) Preparation of Praziguantel

Prazole-5 (0.72 kg), dichloromethane (4.32 L) and sodium carbonate (0.4 kg) were stirred at 25-30° C. for 15 min, cooled to 0-5° C. Cyclohexanoyl chloride (0.54 kg) was added drop-wise, allow the reaction mass to attain 25-30° C. under stirring for 2 hrs. After completion of reaction, reaction mass was quenched to DM water below 30° C., maintain the pH in the range 8-8.5, stirred. Two layers were separated. Aqueous layer was extracted with dichloromethane. Combined organic layers were washed with 1% lye, DM water, dried. Acetone was added, carbon treatment was given to organic layer, stirred for 1 hr at 40-45° C., filtered. Acetone was distilled. Crude material was crystallized by acetone and water, and wash with chilled acetone.

We claim:

1. A process for the preparation of 2-[(2,2-dimethoxyethyl)amino]-N-(2-phenylethyl)acetamide, which comprises:
   a) condensation of β-phenylethylamine with chloroacetyl chloride in the presence of a solvent and a base to obtain 2-chloro-N-phenethylacetamide;
   b) condensation of benzylamine with chloroacetaldehyde dimethylacetal in the presence of water and a base to obtain N-benzyl-2,2-dimethoxyethanamine;
   c) condensation of 2-chloro-N-phenethylacetamide prepared in step a) with N-benzyl-2,2-dimethoxyethanamine of formula VI prepared in step b) in the presence of water and a base to obtain 2-[(2,2-dimethoxyethyl)benzylamino]-N-phenethylacetamide; and
   d) reduction of 2-[(2,2-dimethoxyethyl)benzylamino]-N-phenethylacetamide using a reducing agent and a solvent in the presence of hydrogen to obtain 2-[(2,2-dimethoxyethyl)amino]-N-(2-phenylethyl)acetamide.

2. The process according to claim 1, wherein the solvent in step a) is toluene and the base in step a) is sodium bicarbonate.

3. The process according to claim 1, wherein the base in step b) and step c) is sodium hydroxide.

4. The process according to claim 1, wherein the solvent in step d) is selected from the group consisting of methanol, ethanol, and isopropanol, and the reducing agent in step d) is selected from the group consisting of Raney nickel, platinum, and palladium on carbon.

5. A process for preparation of praziquantel which comprises:
   a) cyclisation of 2-[(2,2-dimethoxyethyl)amino]-N-(2-phenylethyl)acetamide prepared according to claim 1, using an acid in the presence of solvent to obtain 4-oxo-1,2,3,6,7,11b-hexahydro-4H-pyrazino[2,1-a]isoquinoline; and
   b) acylation of 4-oxo-1,2,3,6,7,11b-hexahydro-4H-pyrazino[2,1-a]isoquinoline with cyclohexanoylchloride in presence of a base and a solvent to obtain praziquantel.

6. The process according to claim 5, wherein cyclisation in step a) is carried out in the presence of sulphuric acid and a chlorinated solvent.

7. The process according to claim 5 wherein, acylation in step b) is carried out in presence of sodium carbonate as the base and solvent dichloromethane as the solvent.

8. The process according to claim 5 wherein, the praziquantel obtained in step b) is purified by crystallization from a mixture of acetone and water.

9. The process according to claim 5 wherein, the praziquantel obtained in step b) is purified by crystallization from methanol.

* * * * *